United States Patent [19]

Beach

[11] 3,976,076

[45] Aug. 24, 1976

[54] MEDICAL APPARATUS

[76] Inventor: Janet Beach, P.O. Box 904, Camden, Maine 04843

[22] Filed: June 24, 1974

[21] Appl. No.: 482,160

[52] U.S. Cl.............................. 128/295; 206/494; 4/110
[51] Int. Cl.² ........................................ A61F 5/44
[58] Field of Search................... 128/295, DIG. 24; 4/121, 142, 110; 5/90; 206/69, 494, 527

[56] References Cited
UNITED STATES PATENTS

| | | | |
|---|---|---|---|
| 1,389,531 | 8/1921 | Riche.................................. | 128/295 |
| 3,070,810 | 1/1963 | Jones................................. | 128/295 |
| 3,356,091 | 12/1967 | Patterson............................ | 128/295 |
| 3,392,825 | 7/1968 | Gale et al. .......................... | 206/494 |
| 3,406,690 | 10/1968 | Igel et al............................ | 128/295 |
| 3,452,368 | 7/1969 | Couper.................................. | 4/121 |

Primary Examiner—Robert W. Michell
Assistant Examiner—Henry S. Layton
Attorney, Agent, or Firm—William G. Rhines

[57] ABSTRACT

This invention relates to hospital apparatus, and in one embodiment comprises a urine collector comprising an elongated, substantially cylindrical tube of material which is impermeable to materials produced by the body, said tube being capable of being lapped into a lapped storage configuration, and being retained in open position by reinforcing means integral therewith.

3 Claims, 2 Drawing Figures

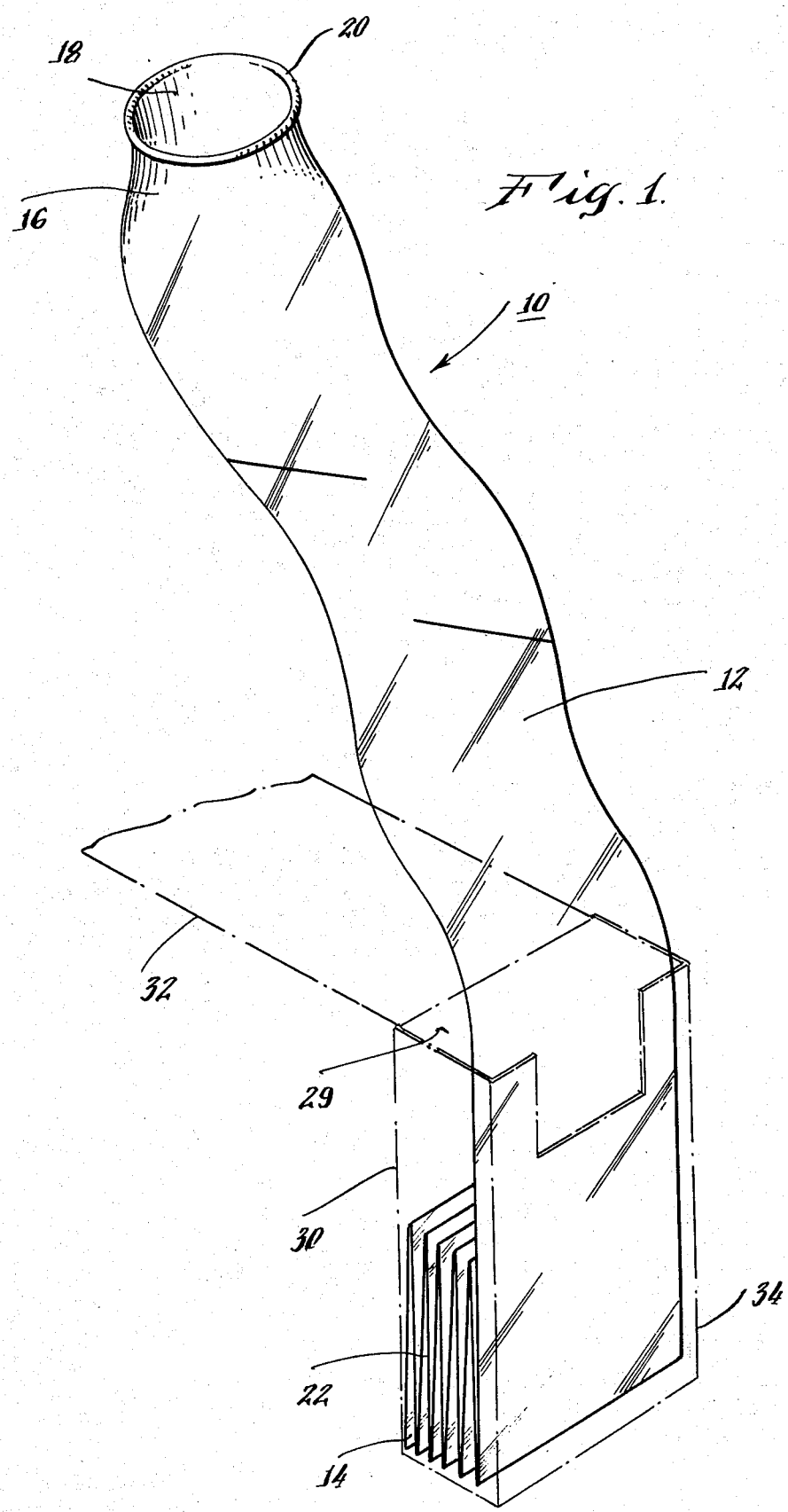

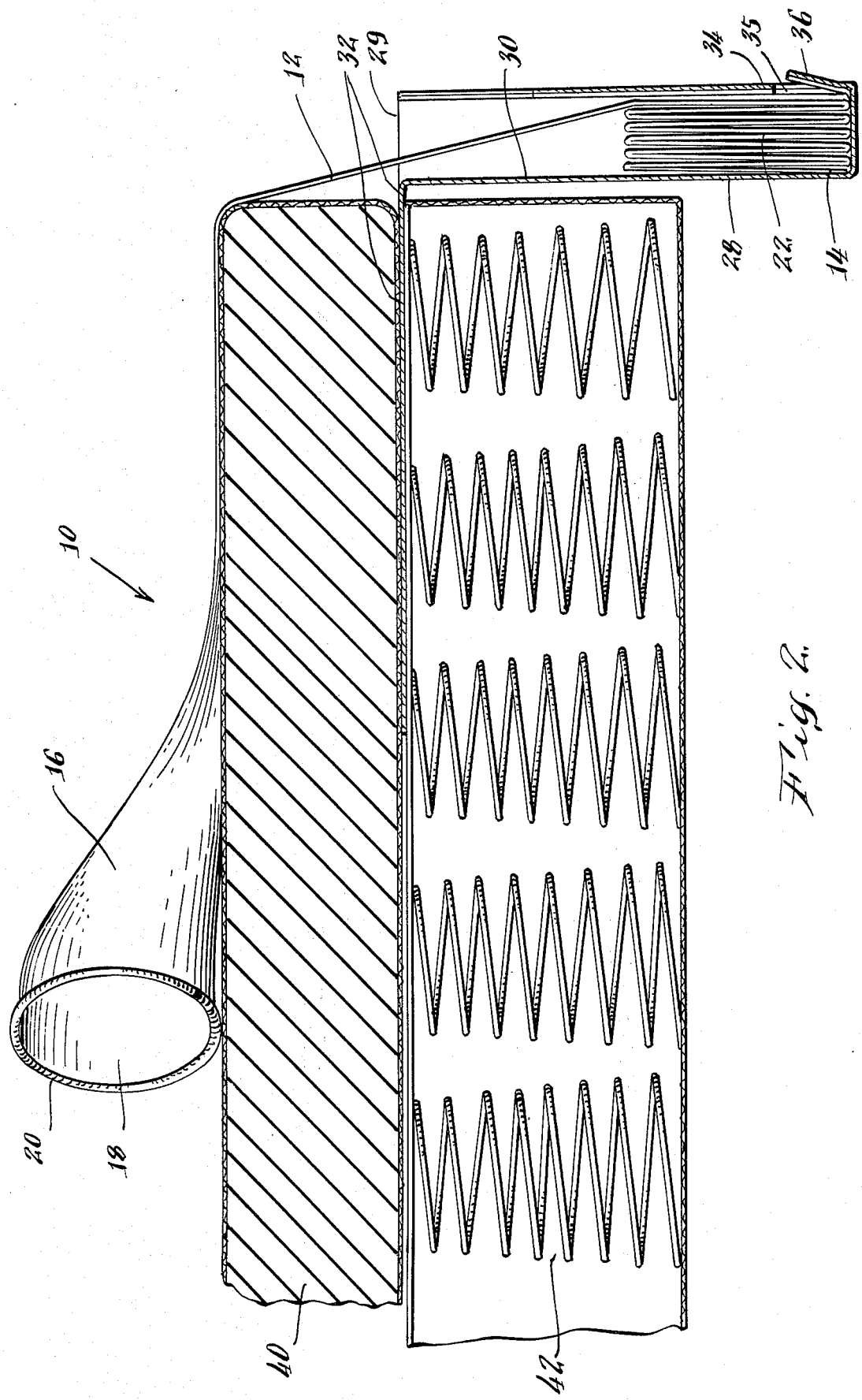

MEDICAL APPARATUS

BACKGROUND OF INVENTION

In the field of hospital apparatus, frequently it is desired to have an inexpensive means for collecting body discharge matter at the bedside. Thus, for example, human male patients who may be very ill, or prone to falling because of being feeble, under the influence of drugs or other medication, or simply weak, may be faced with the necessity of calling for the use of a urinal in order to void, thereby using up the services and time of hospital personnel when they might other wise have traveled to a bathroom to attend their own needs. Hospitals are impelled toward forbidding patients from taking care of themselves because of the hospital's potential liability for personal injuries, and are forced to require that patients use bed-pans and/or other "in-bed" apparatus with all the attendant added costs incurred thereby both for professional personnel and for cleaning the utensils so utilized.

Accordingly, it is an object of the present invention to provide a means whereby hospital patients, and particularly male patients, may attend to their personal evacuation needs.

It is a further object of this invention to provide such means which may be utilized by a patient without the necessity of being attended by hospital personnel.

Another object of this invention is to provide such means that is inexpensive, therefore making it economically feasible to be treated as a "disposable".

SUMMARY OF THE INVENTION

These objects, and others which wll be readily apparent to those skilled in the cognizant arts, may be achieved through practice of the present invention, one embodiment of which is apparatus adapted for collecting urine from bed-ridden male humans comprising an elongated substantially cylindrical, collapsible tube made from material which is substantially impermeable to acqueous liquids, said tube being closed at one end and open at the other end, the walls of said tube at said open end being resiliently biased toward being retained in open position by reinforcing means integral therewith.

DESCRIPTION OF DRAWING

This invention may be more clearly understood from the description which follows and from the attached drawings in which, FIG. 1 illustrates one embodiment of the present invention, and FIG. 2 illustrates one manner of utilizing an embodiment of the present invention, such as that illustrated in FIG. 1.

DESCRIPTION OF PREFERRED EMBODIMENT

Referring first to FIG. 1, there is illustrated apparatus 10 comprising one embodiment of the present invention. This embodiment has a long, cylindrical tube of material, such as latex, rubber or plastic, that is substantially impervious and chemically inert to the material which it is to contain. Thus, for example, if the apparatus is to be used to collect urine, one of the characteristics for which the constituent material of the device should be chosen is substantial imperviousness to acqueous fluids and substantial inertness to the constituent chemicals of urine.

Another characteristic of the material is that it is sufficiently supple to enable it to be flattened and laid back and forth over itself to form laps 22 for storage as a so-called "fan-fold" package as hereinafter described. One end 14 of the tube is sealed shut. This may be done by any of a number of techniques and procedures which are known per se, such as utilizing adhesives, or thermal bonding techniques if the constituent materials are thermoplastic, or by formation with subsequent thermosetting techniques if the constituent material includes natural or artificial rubbers or latexes that are thermosettable. The desirable suppleness of the constituent materials allows the extended main body 12 of the device to lie relatively flat, which is advantageous not only for packaging purposes but also during bed use as hereinafter described.

The other end 16 of the device 10 has an opening 18 through which access may be gained to the interior of the device, thus forming a means by which urine or other fluids may be deposited therein. The opening 18 is biased toward being retained in an open position and at the same time is somewhat resilient so that this bias may be overcome when desired. This may be achieved by a variety of means integral with the device, such as rolling the end of the tube on itself and causing it to be so retained, and/or incorporating a grommet-like configuration of material into the end structure by affixation thereto, molding as an integral part thereof, or rolling the end of the tube over it. This feature facilitates use of the tube, not only to prevent splashing, but also to enable the male genitalia to be retained within the mouth of the tube more or less permanently by a retaining means such as a strap, so that a patient who is incontinent may be serviced.

FIG. 2 illustrates a manner in which an embodiment of the present invention, such as that illustrated in FIG. 1, might be utilized. As illustrated in FIG. 2, the device 10 has been packaged in a box 28 which, when it has been opened at the top 29 so that the main body portion 12 and the end 16 may be removed therefrom, provides a means to retain the lapped or fan-folded portion 22 of the device. The box 28 has a longer back wall 30 which extends into a portion 32 that may be utilized as a top covering for the box when it is closed but, as illustrated, may be bent back to form a readily invertable and removable retaining member 32 suitable to be slid between the mattress 40 and springs 42 of a hospital bed (not shown). The box 22 may also include an outside wall 34, the lower end 35 of which extends below the top of a lip 36 near the bottom end of the box, thereby providing a means whereby the wall 34 may be abutted to the lip 36, and these held in position to provide a cover for the open top 29 before the box is opened.

As noted above, the open end 16 of the device 10 may be drawn out of the box and admitted between the sheets of the bed, and may be held there against becoming "lost" in the bed or dropping out onto the floor by means of a ribbon or other means (not shown) which may be positioned around the outside of the tube in the region of the grommet-like means for holding the end of the tube open. Optionally, of course, a small eyelet (not shown) or a tab (not shown) might be incorporated into the structure in the region of he open end 16, and, as might such means as the aforementioned ribbon. This can provide a means by which the end may be removeably secured to a selected position on one of the sheets and/or the mattress cover.

In use, a male patient, for example, needs only to void into the opening 18 of the tube, which he may conveniently do without having to get out of bed, and when a sufficient volume of fluid has been so introduced into the device, the lapped portion will become available to receive additional amounts of fluid as tube is withdrawn from the box. It will be apparent that the tube may be positioned in the box so that the laps of the fan-holding are oriented vertically rather than horizontally. Since the device so made obviously may be mass produced at a very low cost, it is economically feasible to be disposed of entirely when its use for the same patient is finished.

It is to be understood that the embodiments herein described and illustrated are by way of illustration and not of limitation, and that this invention may be practiced in a wide variety of other embodiments which will be apparent to those skilled in the cognizant arts without departing from the spirit or scope of this invention. For example, the invention is by no means restricted to use by a male, but may also be used by a female as well.

I claim:

1. For use in collecting urine from bed-ridden humans, apparatus comprising a tube made from thin material that is impermeable to acqueous liquids, having one end closed by means of a flat seam, and the other end biased toward being retained open by a grommet-like resilient expander which is integral therewith, said tube other than in the region of said expander being so supple that it will collapse substantially entirely from its own weight when laid on its side, and may be lapped upon itself for storage, said tube being lapped into a fan-fold configuration and positioned within an associated container with said open end of said tube accessible for grasping, whereby desired lengths of said tube may be withdrawn from said container.

2. The apparatus described in claim 1 wherein said material is an elastomer.

3. The apparatus described in claim 2 wherein said material is latex.

* * * * *